US010729829B2

(12) United States Patent
Brown

(10) Patent No.: US 10,729,829 B2
(45) Date of Patent: Aug. 4, 2020

(54) SYSTEMS AND METHODS FOR PLATELET CONCENTRATION WITH A SPINNING MEMBRANE SEPARATOR

(71) Applicant: Fenwal, Inc., Lake Zurich, IL (US)

(72) Inventor: David S. Brown, Lake Barrington, IL (US)

(73) Assignee: Fenwal, Inc., Lake Zurich, IL (US)

( * ) Notice: Subject to any disclaimer, the term of this patent is extended or adjusted under 35 U.S.C. 154(b) by 392 days.

(21) Appl. No.: 15/799,042

(22) Filed: Oct. 31, 2017

(65) Prior Publication Data

US 2018/0133655 A1 May 17, 2018

Related U.S. Application Data

(60) Provisional application No. 62/420,821, filed on Nov. 11, 2016.

(51) Int. Cl.
*A61M 1/02* (2006.01)
*A61M 1/26* (2006.01)
*B01D 63/16* (2006.01)
*B01D 69/02* (2006.01)
(Continued)

(52) U.S. Cl.
CPC .......... *A61M 1/0281* (2013.01); *A61M 1/025* (2013.01); *A61M 1/029* (2013.01); *A61M 1/265* (2014.02); *B01D 63/005* (2013.01); *B01D 63/16* (2013.01); *A61M 2202/0415* (2013.01); *A61M 2202/0427* (2013.01); *A61M 2202/0429* (2013.01); *A61M 2205/50* (2013.01);
(Continued)

(58) Field of Classification Search
CPC ...... B01D 63/16; B01D 63/005; B01D 69/02; B01D 71/50; B01D 2325/04; A61M 1/0281; A61M 1/265; A61M 1/025; A61M 2202/0427; A61M 2202/0415; A61M 2202/50; A61M 2202/0429; A61M 1/029
See application file for complete search history.

(56) References Cited

U.S. PATENT DOCUMENTS 5,034,135 A * 7/1991 Fischel .................. A61M 1/30
 210/321.68
5,194,145 A * 3/1993 Schoendorfer ..... A61M 1/3496
 210/321.63
(Continued)

*Primary Examiner* — John Kim
(74) *Attorney, Agent, or Firm* — Cook Alex Ltd.

(57) ABSTRACT

A method for automated processing of a blood product, the method comprising providing a reusable separation apparatus controlled by a microprocessing unit, said apparatus configurable with settings and configured to associate with a disposable circuit comprising a separator and in communication with a source blood product having a first concentration and first volume. The apparatus and disposable circuit are configured to flow the source blood product into an inlet of the separator and separate supernatant of the source blood product from a first outlet of the separator into a filtrate container. The apparatus and disposable circuit are also configured to separate platelets and remaining supernatant from a second outlet of the separator into a retentate container, wherein the platelets and remaining supernatant in the retentate container have a second concentration greater than the first concentration and second volume less than the first volume.

20 Claims, 5 Drawing Sheets

(51) Int. Cl.
*B01D 71/50* (2006.01)
*B01D 63/00* (2006.01)

(52) U.S. Cl.
CPC .............. *B01D 69/02* (2013.01); *B01D 71/50* (2013.01); *B01D 2325/04* (2013.01)

(56) References Cited

U.S. PATENT DOCUMENTS

| | | | |
|---|---|---|---|
| 5,403,272 A * | 4/1995 | Deniega | A61M 1/30 604/6.03 |
| 6,251,295 B1 * | 6/2001 | Johnson | A61M 1/3621 210/650 |
| 6,419,822 B2 | 7/2002 | Muller et al. | |
| 9,381,291 B2 | 7/2016 | Boggs et al. | |

* cited by examiner

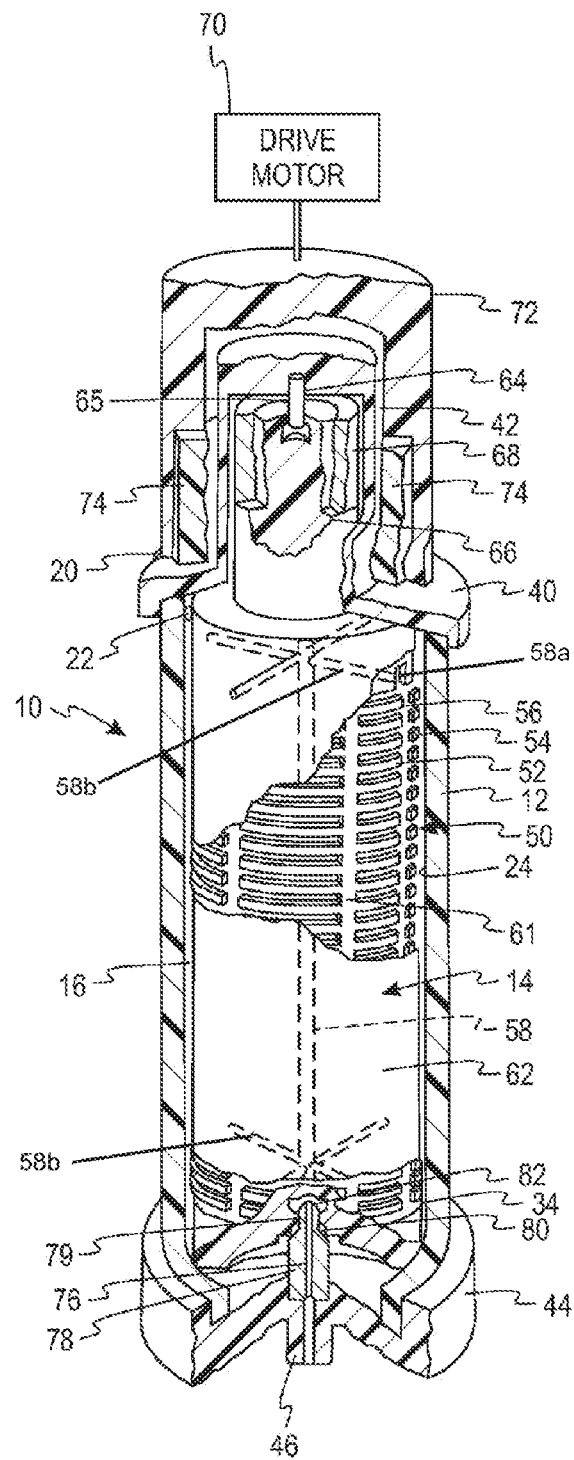
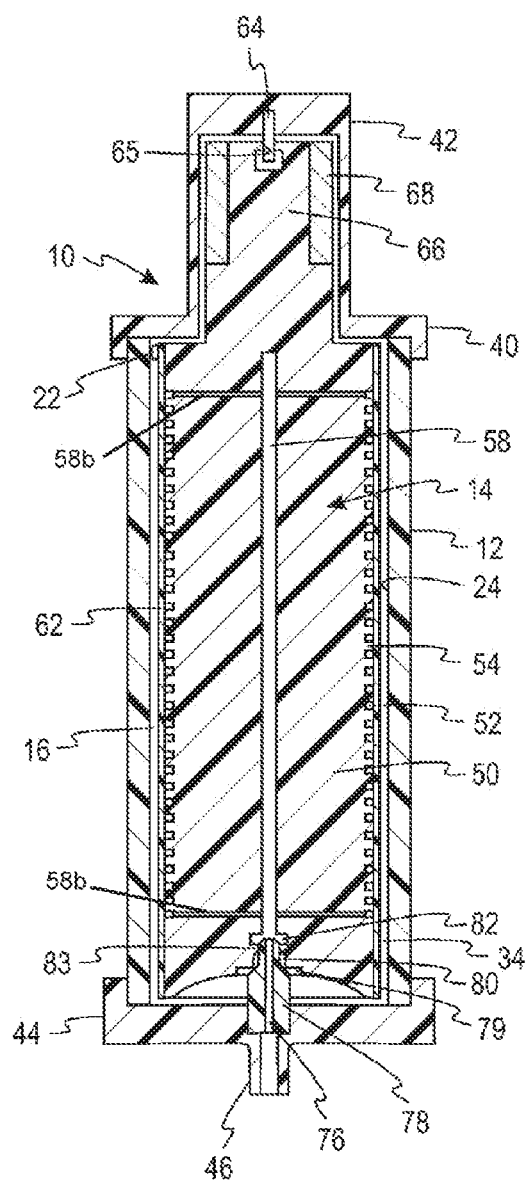
FIG. 1
FIG. 2

SYSTEMS AND METHODS FOR PLATELET CONCENTRATION WITH A SPINNING MEMBRANE SEPARATOR

CROSS-REFERENCE TO RELATED APPLICATIONS

This application claims the benefit of U.S. Provisional Patent App. No. 62/420,821 filed Nov. 11, 2016, which is expressly incorporated herein by reference in its entirety.

FIELD OF THE DISCLOSURE

The present disclosure is directed to separation devices of the type employing relatively rotating surfaces, at least one of which carries a membrane for filtering a component from fluid passed between the surfaces.

BACKGROUND

Different types of blood collection procedures exist, including manual collection of whole blood from healthy donors through blood drives, donor visits to blood centers or hospitals and the like. In typical manual collection, whole blood is collected by simply flowing it, under the force of gravity and venous pressure, from the vein of the donor into a collection container. The amount of whole blood drawn is typically a "unit," which is about 450 to 550 mL.

Collection may employ a pre-assembled arrangement of tubing and containers or bags, including a flexible plastic primary container or bag for receiving a unit of whole blood from a donor and one or more "satellite" containers or bags. The blood may first be collected in the primary container, which also contains an anticoagulant (typically containing sodium citrate, phosphate and dextrose-often referred to as CPD). A preservative (often called an "additive solution" or AS, and commonly containing a saline, adenine and glucose medium-which is referred to as SAG) may be included as part of a larger assembly of containers and tubes that are used in processing after the blood is collected.

After collection of a unit of whole blood, the unit of whole blood, with connected tubing and containers, may be transported to a blood component processing laboratory, commonly referred to as a "back lab," for further processing. Further processing may entail loading the primary container and associated tubing and satellite containers into a centrifuge to separate the whole blood into components such as concentrated red cells and platelet-rich or platelet-poor plasma. These components are then manually expressed from the primary container into other pre-connected satellite containers, and may again be centrifuged to separate the platelets from plasma. Subsequently, the blood components may be leukoreduced by filtration for further processing or storage. The process may be time-consuming, labor intensive, and subject to possible human error.

Blood banks and transfusion centers may also perform the task of "cell washing," which removes and/or replaces the liquid medium (or a part thereof) in which the cells are suspended, to concentrate or further concentrate cells in a liquid medium, and/or to purify a cell suspension by the removal of unwanted cellular or other material.

Cell washing systems may involve centrifugation of a cell-suspension, decanting of the supernatant, re-suspension of concentrated cells in new media, and possible repetition of these steps until the cells of the suspension are provided at an adequately high or otherwise desirable concentration. Centrifugal separators used in the processing of blood and blood components may be used in such cell-washing methods.

Blood separation apparatus and procedures may employ a separation membrane to separate blood components instead of a centrifuge. This type of device includes relatively rotating surfaces, at least one or which carries a porous membrane. The device may have an outer stationary housing and an internal spinning rotor covered by a porous membrane.

SUMMARY

According to an exemplary embodiment, the present disclosure is directed to a system for automated processing of a blood product, the system comprising a reusable separation apparatus controlled by a microprocessing controller unit driven by software, wherein the apparatus and microprocessing controller unit are configurable with a plurality of settings. The system also comprises a disposable sterile circuit configured to associate with the reusable separation apparatus, and the disposable sterile circuit comprises a spinning membrane separator comprising a porous membrane, wherein the separator comprises an inlet and first and second outlets. The system also comprises a source blood product having a first concentration and first volume in communication with the inlet of the separator, wherein the separation apparatus is configured by the microprocessing controller to flow the source blood product into the inlet of the separator, separate an amount of supernatant of the source blood product from the first outlet into a filtrate container, and separate platelets and remaining supernatant from the second outlet into a retentate container. The separation apparatus is configured by the microprocessing controller to collect the platelets and remaining supernatant in the retentate container at a second concentration and second volume, wherein the second concentration is greater than the first concentration and the second volume is less than the first volume.

According to an exemplary embodiment, the present disclosure is directed to a method for automated processing of a blood product, the method comprising providing a reusable separation apparatus controlled by a microprocessing unit driven by software, said apparatus configurable with a plurality of settings and configured to associate with a disposable sterile circuit comprising a separator comprising a porous membrane and in communication with a source blood product having a first concentration and first volume. The apparatus and disposable sterile circuit are configured to flow the source blood product into an inlet of the separator and separate an amount of supernatant of the source blood product from a first outlet of the separator into a filtrate container. The apparatus and disposable sterile circuit are also configured to separate platelets and remaining supernatant from a second outlet of the separator into a retentate container, wherein the platelets and remaining supernatant in the retentate container have a second concentration and second volume. The second concentration is greater than the first concentration and the second volume is less than the first volume.

According to an exemplary embodiment, the present disclosure is directed to a method for automated processing of a blood product, the method comprising providing a reusable separation apparatus controlled by a microprocessing unit driven by software, said apparatus configurable with a plurality of settings and configured to associate with a disposable sterile circuit comprising a separator comprising a porous membrane and in communication with a source blood product. The apparatus and disposable sterile circuit are configured to flow the source blood product into an inlet of the separator and separate an amount of plasma and platelets of the source blood product from a first outlet of the separator into a first container, wherein the amount of plasma and platelets collected in the first container has a first platelet concentration and first volume. The apparatus and disposable sterile circuit are also configured to separate red blood cells from a second outlet of the separator into a second container, flow the plasma and platelets derived from the first container into the inlet of the separator, separate an amount of plasma from the first outlet of the separator, and separate platelets and remaining plasma from the second outlet of the separator into a third container, wherein the platelets and remaining supernatant in the third container have a second platelet concentration and second volume. The second platelet concentration is greater than the first concentration and the second volume is less than the first volume.

BRIEF DESCRIPTION OF THE DRAWINGS

Features, aspects, and advantages of the present embodiments will become apparent from the following description, appended claims, and the accompanying exemplary embodiments shown in the drawings, which are briefly described below.

FIG. 1 is a perspective view a spinning membrane separator, in partial cross section and with portions removed to show detail, according to an exemplary embodiment;

FIG. 2 is a longitudinal cross sectional view of the spinning membrane separator of FIG. 1, according to an exemplary embodiment;

DETAILED DESCRIPTION

Figure 3:
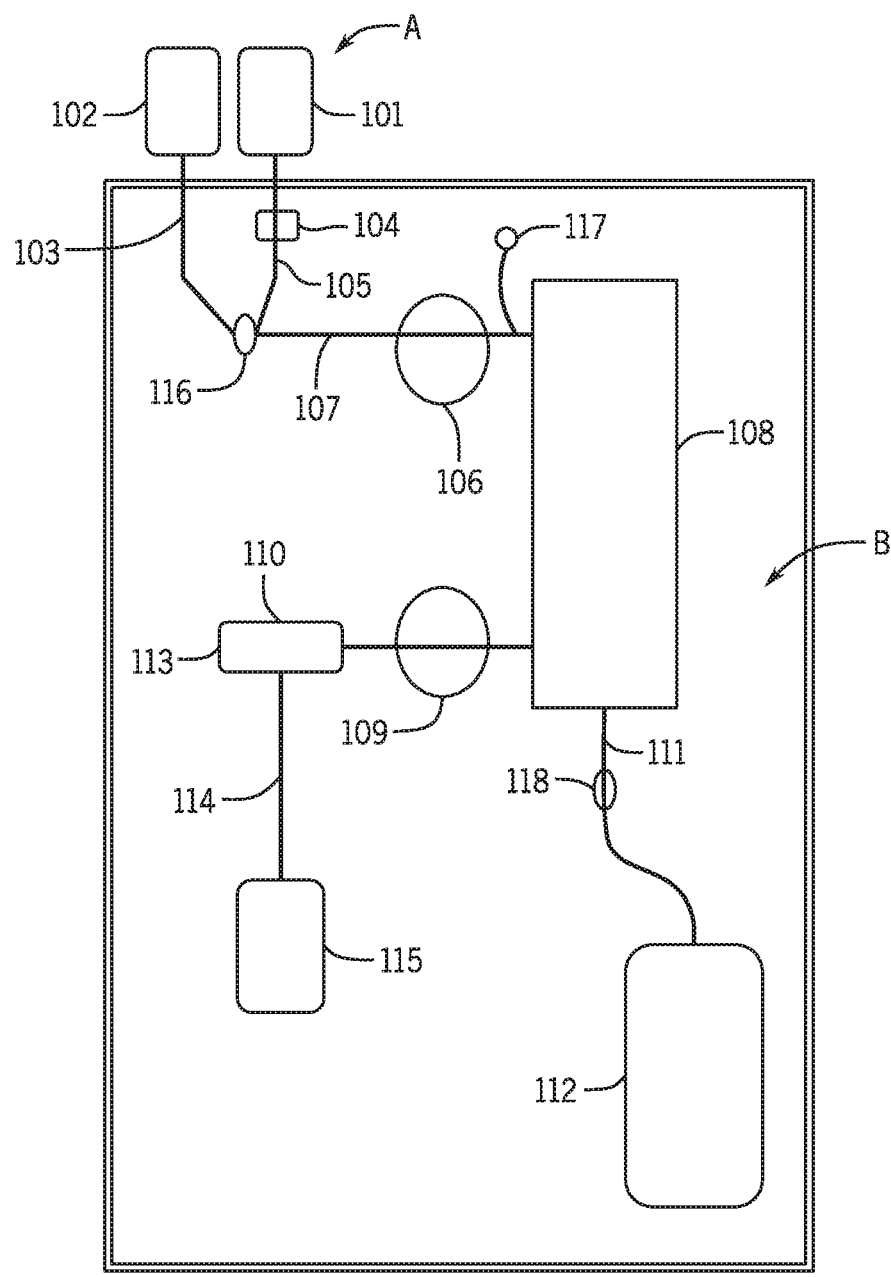
FIG. 3 is a schematic view of an automated blood separation system for processing blood including a disposable fluid flow circuit module and a durable controller or control module with the fluid flow circuit module assembled thereon, according to an exemplary embodiment.

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

A description of a spinning membrane separator may be found in U.S. Pat. No. 9,381,291, which is incorporated by reference herein in its entirety, and describes a membrane-covered spinner having an interior collection system disposed within a stationary shell. Blood is fed into an annular space or gap between the spinner and the shell. The blood moves along the longitudinal axis of the shell toward an exit region, with plasma passing through the membrane and out of the shell into a collection container. The remaining blood components, primarily red blood cells, platelets and white cells, move to the exit region between the spinner and the shell and may be returned to the donor or collected for further processing.

Spinning membrane separators may provide excellent filtration rates, due primarily to the unique flow patterns ("Taylor vortices") induced in the gap between the spinning membrane and the shell. The Taylor vortices help to keep the blood cells from depositing on and fouling or clogging the membrane.

Turning to FIGS. 1 and 2, a spinning membrane blood separation or fractionation system, generally designated 10, is shown. Such a system 10 may be used to extract plasma and red blood cells from whole blood obtained from a donor. Only the separation device and the associated drive unit are shown, but it should be understood that such a separator may be part of a disposable system including collection containers, containers of additives such as saline, SAG, or ACD, return containers, tubing, etc., and that there are also associated control and instrumentation systems for operation of the device.

The system 10 may include a generally cylindrical housing 12, mounted concentrically about a longitudinal vertical central axis. An internal member 14 may be mounted concentric with the central axis. The housing and internal member are relatively rotatable. The housing 12 may be stationary and the internal member 14 may be a rotating spinner that is rotatable concentrically within the cylindrical housing 12. The boundaries of the blood flow path may generally be defined by the gap 16 between the interior surface of the housing 12 and the exterior surface of the rotary spinner 14. The spacing between the housing 12 and the spinner 14 can be referred to as the shear gap. A typical shear gap may be approximately 0.025-0.050 inches (0.067-0.127 cm) and may be of a uniform dimension along the axis, for example, where the axis of the spinner and housing are coincident. The shear gap may also vary circumferentially for example, where the axis of the housing and spinner are offset.

The shear gap 16 may vary along the axial direction. For example, an increasing gap width in the direction of flow may be implemented to limit hemolysis. Such a gap width may range from about 0.025 to about 0.075 inches (0.06-0.19 cm). For example, the axes of the housing 12 and rotor 14 could be coincident and the diameter of the rotor 14 decrease in the axial direction (direction of flow) while the diameter of inner surface of the housing 12 remains constant or the diameter of the housing 12 increases while the rotor 14 diameter remains constant, or both surfaces vary in diameter. The gap width may be varied by varying the outer diameter of the rotor 14 and/or the inner diameter of the facing housing surface. The width dimension of the gap 16 may be selected so that at the desired relative rotational speed, Taylor-Couette flow, such as Taylor vortices, are created in the gap and hemolysis is limited.

Referring to FIGS. 1 and 2, whole blood may be fed from an inlet conduit 20 through an inlet orifice 22, which directs the blood into the blood flow entrance region in a path tangential to the circumference about the upper end of the spinner 14. At the bottom end of the cylindrical housing 12, the housing inner wall includes an exit orifice 34. The cylindrical housing 12 may be completed by an upper end cap 40 and a bottom end housing 44 terminating in a plasma outlet orifice 46 concentric with the central axis.

The spinner 14 may be rotatably mounted between the upper end cap 40 and the bottom end housing 44. The spinner 14 may comprise a shaped central mandrel or rotor 50, the outer surface of which may be shaped to define a series of spaced-apart circumferential grooves or ribs 52 separated by annular lands 54. The surface channels defined by the circumferential grooves 52 may be interconnected by longitudinal grooves 56. At one or more ends of the mandrel 50, these grooves 56 may be in communication with a central orifice or manifold 58 via an opening 58a and bridge 58b.

The surface of the rotary spinner 14 may be at least partially or entirely covered by a cylindrical porous membrane 62. The membrane 62 may have a nominal pore size of 0.6 microns, although other pore sizes may alternatively be used. In one embodiment, pore sizes in the range of 0.2 microns to 5 microns may be used. "Pore size" generally refers to the cross-sectional dimension of the pore 24, and not the depth of the pore 24 through the filter layer. For both pores of circular and non-circular shapes, "pore size" generally refers to the smallest cross-sectional dimension of the pores, unless otherwise stated. The membrane 62 may be a fibrous mesh membrane, cast membrane, track-etched membrane, etc. For example, the membrane 62 may have a polyester mesh (substrate) with nylon particles solidified thereon, thereby creating a tortuous path through which only certain sized components will pass. In another embodiment, the membrane may be made of a thin (e.g., approximately 0.5-15 microns thick) sheet of, for example, polycarbonate, nylon, and/or both, and pores may be, e.g., approximately 3-5 microns. The pores may be sized to allow small formed components (e.g., platelets, microparticles, etc.) to pass, while the desired cells (e.g., red and/or white blood cells) are collected. In another embodiment, the membrane thickness may be in the range of 10 to 190 microns and have any suitable pore size from 0.2 microns to 5 microns.

The rotary spinner 14 may be mounted in the upper end cap 40 to rotate about a pin 64, which may be press fit into the end cap 40 on one side and seated within a cylindrical bearing surface 65 in an end cylinder 66 forming part of the rotary spinner 14. The internal spinner 14 or outer housing 12 may be rotated by any suitable rotary drive device or system. The end cylinder 66 may be partially encompassed by a ring 68 of magnetic material utilized in indirect driving of the spinner 14. A drive motor 70 exterior to the housing 12 may be coupled to turn an annular magnetic drive member 72 that includes at least a pair of interior permanent magnets 74. As the annular drive member 72 is rotated, magnetic attraction between the ring 68 interior to the housing 12 and the magnets 74 exterior to the housing may lock the spinner 14 to the exterior drive, causing the spinner 14 to rotate.

At the lower end of the rotary spinner 14, the central outlet orifice 58 may communicate with a central bore 76 in an end bearing 78 that is concentric with the central axis. An end bearing seat may be defined by an internal shoulder 80 that forms a lower edge of a central opening 82, which communicates with the plasma outlet orifice 46.

A spinning membrane separation device as described above may be advantageously used in various blood processing systems and methods. In one embodiment, a spinning membrane separation device may be used for obtaining red blood cells (RBCs) and/or washing and obtaining platelets.

Some embodiments may allow for efficient washing and/or concentration of platelets with minimized platelet activation.

In some embodiments, the spinner may be used for "back lab" processing of previously collected whole blood or previously collected platelets.

Some embodiments may allow for achieving target platelet concentrations with minimal fouling of the spinning membrane.

Turning now to FIG. 3, a disposable fluid flow circuit or module A and a reusable durable controller or module B configured to cooperate with and control flow through the fluid circuit A are schematically illustrated. The disposable fluid circuit A as illustrated in FIG. 3 may include various components interconnected by flexible plastic tubing defining flow paths between the components. The disposable circuit in FIG. 3 may include source container 101, a solution container 102, blood component separator 108, plasma collection container 112, optional leukocyte reduction filter 113, and collection container 115. While not illustrated in FIG. 3, the reusable module B may have hangers with associated weigh scales for supporting any or all of the containers 101, 102, 112 and 115.

The source container 101 may be any suitable container but is typically a flexible plastic pouch or bag in which a volume of whole blood or blood component(s) have been previously collected. In the case of whole blood, approximately 450 ml (a typical "unit") of whole blood may have been previously collected. The container 101 may be part of a separate system during collection and then joined to the rest of the fluid circuit A or actually part of the circuit A at the time of collection. In the case in which source container 101 contains whole blood, at the time of collection, in accordance with customary procedure, the whole blood may be mixed with an anticoagulant to prevent premature coagulation. Accordingly, "Whole blood" as used herein includes blood mixed with anticoagulant.

Flexible plastic tubing 105 may be attached to the source container, such as by a sterile connection device or other suitable attachment mechanism, and defines a source fluid flow path between the source container 101 and a junction with cell preservative or wash solution tubing 103, which extends from the cell preservative/wash solution container 102 to the flow path junction. The flow path junction between the source flow path and cell preservative/wash flow path may be located at inlet clamp 116. From the junction, the flow path may extend through tubing 107 to an inlet port in the separator 108.

As shown in FIG. 3 of this description, the separator housing has an outlet that communicates with the gap between the housing and rotor and with retentate flow path tubing 110 for withdrawing retentate from the separator gap. In one embodiment, the retentate may be concentrated red blood cells. In addition, the housing includes an outlet from the rotor that communicates with the side of the membrane facing away from the gap (for example, the interior of the rotor) and communicates with filtrate flow path tubing 111. In one embodiment, the filtrate may be plasma.

The disposable fluid flow circuit A may optionally include a leukocyte reduction filter 113 if it is desired to remove leukocytes that may be present in the red blood cells in the case in which retentate is RBCs. The retentate may flow from the leukocyte reduction filter 113 through a continuation 114 of the retentate flow path into storage container 115, which may be of any suitable plastic material compatible with cell storage.

The reusable or durable controller module B, as shown in the FIG. 3 schematic, may preferably include an optical sensor 104 for detecting, for example, hematocrit of the blood component(s) flowing from the source container 101, or concentration of the fluid flowing from the source container 101. An example of an optical sensor is described in U.S. Pat. No. 6,419,822, which is incorporated by reference in its entirety, although the optical sensor may be of any suitable design or construction.

The durable reusable controller or control module B may also include an inlet clamp 116 which may be operated to control fluid from the source container 101 or the cell preservative/wash container 102 or, optionally, simultaneously and proportionally from both of the containers 101 and 102. For controlling flow of source fluid into the separator, the reusable module may include an inlet pump 106, which also may be of any suitable construction, and may be, for example, a peristaltic type pump which operates by progressive compression or squeezing of the tubing 107 forming the inlet flow path into the separator, a flexible diaphragm pump, or other suitable pump. A pressure sensor 117 may communicate with the inlet flow path between the pump 106 and the separator 108 to determine the inlet pumping pressure. The sensor 117 may output to the control system to provide an alarm function in the event of an over-pressure condition or an under-pressure condition or both.

To control the flow rate of retentate from the separator 108, the reusable module may also include an outlet pump 109 that is associated with the outlet flow path 110, and may function in the manner similar to that described with respect to inlet pump 106. Outlet pump 109 also may be of any suitable construction such as a peristaltic pump, a flexible diaphragm, or other suitable pumping structure. In one embodiment, the filtrate flow path 111 exiting the separator is not controlled by a pump, and the volumetric flow rate through the plasma flow path tubing 111 is the difference between the inlet volumetric flow rate from pump 106 and the outlet volumetric flow rate from pump 109. Reusable module B may, however, include a clamp 118 for controlling flow of plasma through the plasma flow path tubing 111.

The disposable module A may include a filtrate collection container 112 in fluid communication with the filtrate flow path for receiving filtrate separated by the separator 108. In an embodiment in which the filtrate is plasma, because the plasma passes through a porous membrane in the separator 108, the plasma that is collected in container 112 may be largely cell free plasma and may be suitable for administration to patients, freezing for storage, or subsequent processing.

The durable controller may comprise a microprocessing unit driven by software, with certain steps performed by a human operator/user. For example, the controller, when switched on, may conduct self-calibration checks, including the checking of the peristaltic pumps, clamps, and sensors. The controller may then prompt the user to enter selected procedural parameters, such as the fluid procedure to be performed, the amount of fluid to be processed, the number of procedures to take place, etc. The operator may then select and enter the procedural parameters for the fluid procedure.

The microprocessing unit may calculate the volume of wash solution needed for the procedure based on a "maximum output concentration" for the separator, defined as the maximum ratio of the volume of cellular material to the volume of the total suspension that can be processed by the separator without losing cells of interest. The maximum output concentration may be a function of factors such as the configuration of the membrane, the pore size, and speed of rotation of the membrane. This may be determined or derived empirically for a particular spinner configuration, and pre-programmed into the microprocessor, or a value may be input by the system operator.

A "concentration ratio," defined as the ratio of the volume of the input to the separator to the output of the separator for the procedure, may be determined. This value may be directly inputted into the controller by the system operator, or it may be automatically determined by the controller based on other operator input selections. The input to the separator may be determined by a "spinner inlet flow rate" that may be set by an operator or configured automatically. The output of the separator may be determined by a "reduction retentate pump rate" (also called "spinner outlet flow rate") that may likewise be set by an operator or configured automatically.

A "maximum input concentration," also called "desired inlet spinner packed cell volume (PCV)," may be determined as a function of the maximum output concentration and the concentration ratio, specifically the maximum output concentration divided by the concentration ratio. The desired inlet spinner PCV may indicate the maximum density of cells allowed to enter the separator module to manage the density of cells that exit the spinner. The desired inlet spinner PCV may be set by an operator. During the washing procedure, washing solution may be added to the cells to be washed in an amount so that the cellular concentration of the input to the separator does not exceed the maximum input concentration. By way of example, if the maximum output concentration is 30% and cell products are to be washed, for which the concentration ratio is 10:1, the maximum input concentration is 30%÷10=3%. Thus the volume of wash solution necessary for the procedure should be sufficient to dilute the suspension being input to the separator to a 3% cellular concentration, resulting in an output concentration that does not exceed 30%, and a container containing at least this volume of wash solution should be connected to the disposable set prior to the start of the wash procedure.

A "spinner revolution rate" may be described in revolutions per minute (rpm) and is a measurement of how fast the spinner is spinning. The spinner revolution rate of the spinner may affect how tight the Taylor vortices and how closely target cells reach the membrane. Higher spinner revolution rates may lead to tighter Taylor vortices, leading to decreased mean size of cells retained (not passing through the membrane), and lower spinner revolution rates may allow cells to spread closer to the membrane, leading to increased mean size of cells retained (not passing through the membrane).

A disposable fluid flow circuit and a reusable durable controller as described above may also be used in washing, collection, and/or concentration of platelets. In one embodiment, the platelets to be processed may have been previously collected at a separate location/time. In another embodiment, the platelets to be processed may be a product collected from container 112 or 115 above to be used as the source fluid.

A study was conducted in order to determine and evaluate parameters for platelet processing. One object of the study was to identify parameters allowing the above system to wash and concentrate platelets to achieve a 10:1 concentration ratio while maintaining the platelets in a measurable retentate volume. Another object of the study was to determine whether the target 10:1 concentration ratio is suitable for membrane separator 108 to operate below its concentration polarization limit at a spinner revolution rate that is low enough not to activate platelets.

A standard platelet unit contains approximately $3_E11$ platelets in 250 mL total suspension ($300_E3$ platelets/uL), and a 10:1 concentration ratio would yield $3000_E3$ platelets/uL. In the study, six same-type partial platelet units were pooled together. The total volume of the pooled platelets was 435 mL, and the measured platelet concentration was $1228_E3$ platelets/uL, resulting in a total platelet count of $50.34_E11$ platelets. In order to achieve an initial concentration similar to that of a standard platelet unit (~$300_E3$ platelets/uL), approximately 1346 mL of saline was added to the 435 mL of pooled platelets to result in a concentration of approximately $300_E3$ platelets/uL and a total volume of approximately 1780 mL. The diluted platelet pool was then split into two batches of approximately 890 mL each.

The following parameters were utilized for the study. Although multiple target retentate platelet concentration values were studied, a baseline target retentate platelet concentration value of 1000e3 plt/uL was selected. The target retentate concentration value represents the desired final concentration of the final platelet product collected in container 115 of FIG. 3. A target retentate pump rate value of 8 mL/min was selected. The target retentate pump rate represents the outlet volumetric flow rate from pump 109 pumping retentate from the separator 108 to the collection container 115. A spinner revolution rate (rate of rotation of separator) of 2500 rpm was selected.

With the aforementioned parameters, the two platelet batches were processed individually and separately through a disposable fluid flow circuit A and durable controller module B of FIG. 3. The separator 108 used for the study utilized a 0.6 micron polycarbonate membrane.

Each platelet concentration procedure was optimized by initial priming, a process by which the surface area of the filter membrane is wetted, thus maximizing the membrane area available for filtration/separation. It has been found that introducing priming fluid into the separator so that it works against the force of gravity as the fluid-air interface advances in an upward direction across the surface of the membrane provides a more uniform air-fluid interface and improves uniform wetting of the membrane surface. To that end, with reference to FIGS. 1-3, the priming solution may be introduced from container 101 or 102 through one of the exit orifice 34 or plasma outlet orifice 46 of the spinning membrane separator 10, while air is expelled through the inlet orifice 22. Alternatively, separator 10 may be inverted or upturned for priming, so that the exit orifice 34 and plasma outlet orifice 46 are at the top of the separator 10, and the inlet orifice 22 is at the bottom of the separator 10. The priming solution may then be introduced through the inlet 22, with the fluid-air interface advancing upwardly and air being expelled through either or both of the exit orifice 34 and the plasma outlet orifice 46. After priming, the separator 10 may be returned to its original orientation, with the inlet orifice 22 at the top and the exit orifice 34 and plasma outlet orifice 46 at the bottom.

Each platelet batch underwent a separation procedure. Each of the two platelet batches was placed in source container 101. Filtrate clamp 118 was opened, and the retentate pump rate was set to 8 mL/min appropriate for the baseline target retentate platelet concentration of 1000 plt/uL. Samples were taken approximately every 20 seconds from both the retentate flowing towards retentate container 115 and filtrate leaving the spinner 108. Each retentate sample of 1 mL was taken from between the retentate pump 109 and retentate bag 115 to minimize disruption to fluid flow rate control. Each filtrate sample of 2 mL was taken from the filtrate port 46 of the spinner 10. Throughout the procedure, the target retentate platelet concentration value was step-wise increased and samples collected throughout. Given that concentration ratio (and target retentate platelet concentration) is a function of spinner inlet flow rate and reduction retentate pump rate, and given that reduction retentate flow rate has been fixed at 8 mL/min and concentration ratio has been fixed at step-wise target rates, spinner inlet flow rate values were calculated for each target retentate platelet concentration to achieve each target retentate platelet concentration. The spinner inlet flow rate is determined by the volumetric rate of the source pump 106, and therefore, for each target retentate platelet concentration value, the rate of the source pump 106 was configured into the controller.

Run 1—Batch #1 Having Platelet Concentration of 245e3 plt/uL in 890 mL Total Suspension

TABLE A

| | Target Retentate Platelet Concentration (1e3plt/uL) | | | |
|---|---|---|---|---|
| Starting source of platelets: Concentration of 245e3plt/uL in 890 mL | 1000 (starting target) | 1500 ($2^{nd}$ target) | 2000 ($3^{rd}$ target) | 3000 ($4^{th}$ target) |
| Target source pump rate (mL/min) | 32.7 | 49 | 75.3 | 100 |
| Target retentate pump rate (mL/min) | 8 | 8 | 8 | 8 |
| Spinner revolution rate (rpm) | 2500 | 2500 | 2500 | 2500 |
| Actual % Plasma Removal | 76% | 84% | 88% | 92% |
| Total Fluid Volume Processed (mL) | 98 | 245 | 441 | 980 |

Table A lists parameters and results from the study for the first batch of platelets. Starting with an initial source concentration of 245e3 platelets/uL in a total volume of 890 mL in container 101 of FIG. 3, the durable controller entered the first phase of the procedure to concentrate a portion of the first batch into 1000e3 platelets/uL. At all phases and target retentate concentration values, the retentate pump rate was set to 8 ml/min and spinner revolution rate to 2500 rpm. In the first phase, the source pump rate was set to 32.7 mL/min. A total fluid volume of 98 mL was processed and actual filtrate removal rate was 76%. The durable controller then entered the second phase of the procedure to concentrate a portion of the batch into 1500e3 platelets/uL. In the second phase, the source pump rate was set to 49 mL/min. A total fluid volume of 245 mL was processed and actual filtrate removal rate was 84%. The durable controller then entered the third phase of the procedure to concentrate a portion of the batch into 2000e3 platelets/uL. In the third phase, the source pump rate was set to 75.3 mL/min. A total fluid volume of 441 mL was processed and actual filtrate removal rate was 88%. The durable controller then entered the fourth phase of the procedure to concentrate a portion of the batch into 3000e3 platelets/uL. In the fourth phase, the source pump rate was set to 100 mL/min. A total fluid volume of 980 mL was processed and actual filtrate removal rate was 92%. At each phase, retentate and filtrate samples were collected.

Run 2—Batch #2 Having Platelet Concentration of 280e3 plt/uL in 890 mL Total Suspension

TABLE B

| | Target Retentate Platelet Concentration (1e3plt/uL) | | | |
|---|---|---|---|---|
| Starting source of platelets: Concentration of 280e3plt/uL in 890 mL | 1000 (starting target) | 1500 ($2^{nd}$ target) | 2000 ($3^{rd}$ target) | 3000 ($4^{th}$ target) |
| Target source pump rate (mL/min) | 35.7 | 53.6 | 71.4 | 107.1 |

TABLE B-continued

| | Target Retentate Platelet Concentration (1e3plt/uL) | | | |
|---|---|---|---|---|
| Starting source of platelets: Concentration of 280e3plt/uL in 890 mL | 1000 (starting target) | 1500 ($2^{nd}$ target) | 2000 ($3^{rd}$ target) | 3000 ($4^{th}$ target) |
| Target retentate pump rate (mL/min) | 10 | 10 | 10 | 10 |
| Spinner revolution rate (rpm) | 2500 | 2500 | 2500 | 2500 |

Table B lists the parameters used to run the study for the second batch of platelets. Starting with an initial source concentration of 280e3 platelets/uL in a total volume of 890 mL in container 101 of FIG. 3, the durable controller entered the first phase of the procedure to concentrate a portion of the first batch into 1000e3 platelets/uL. At all phases and target retentate concentration values, the retentate pump rate was set to 10 ml/min and spinner revolution rate to 2500 rpm. For Run 2, target retentate pump rate was changed from 8 mL/min to 10 mL/min in order to test higher filtrate flow rates at the spinner speed of 2500 rpm. In the first phase, the source pump rate was set to 35.7 mL/min. The durable controller then entered the second phase of the procedure to concentrate a portion of the batch into 1500e3 platelets/uL. In the second phase, the source pump rate was set to 53.6 mL/min. The durable controller then entered the third phase of the procedure to concentrate a portion of the batch into 2000e3 platelets/uL. In the third phase, the source pump rate was set to 71.4 mL/min. The durable controller then entered the fourth phase of the procedure to concentrate a portion of the batch into 3000e3 platelets/uL. In the fourth phase, the source pump rate was set to 107.1 mL/min. At each phase, retentate and filtrate samples were collected.

It was observed that for both Runs #1 and #2, actual retentate platelet concentrations achieved or neared target retentate platelet concentrations at all phases.

Figure 4A:
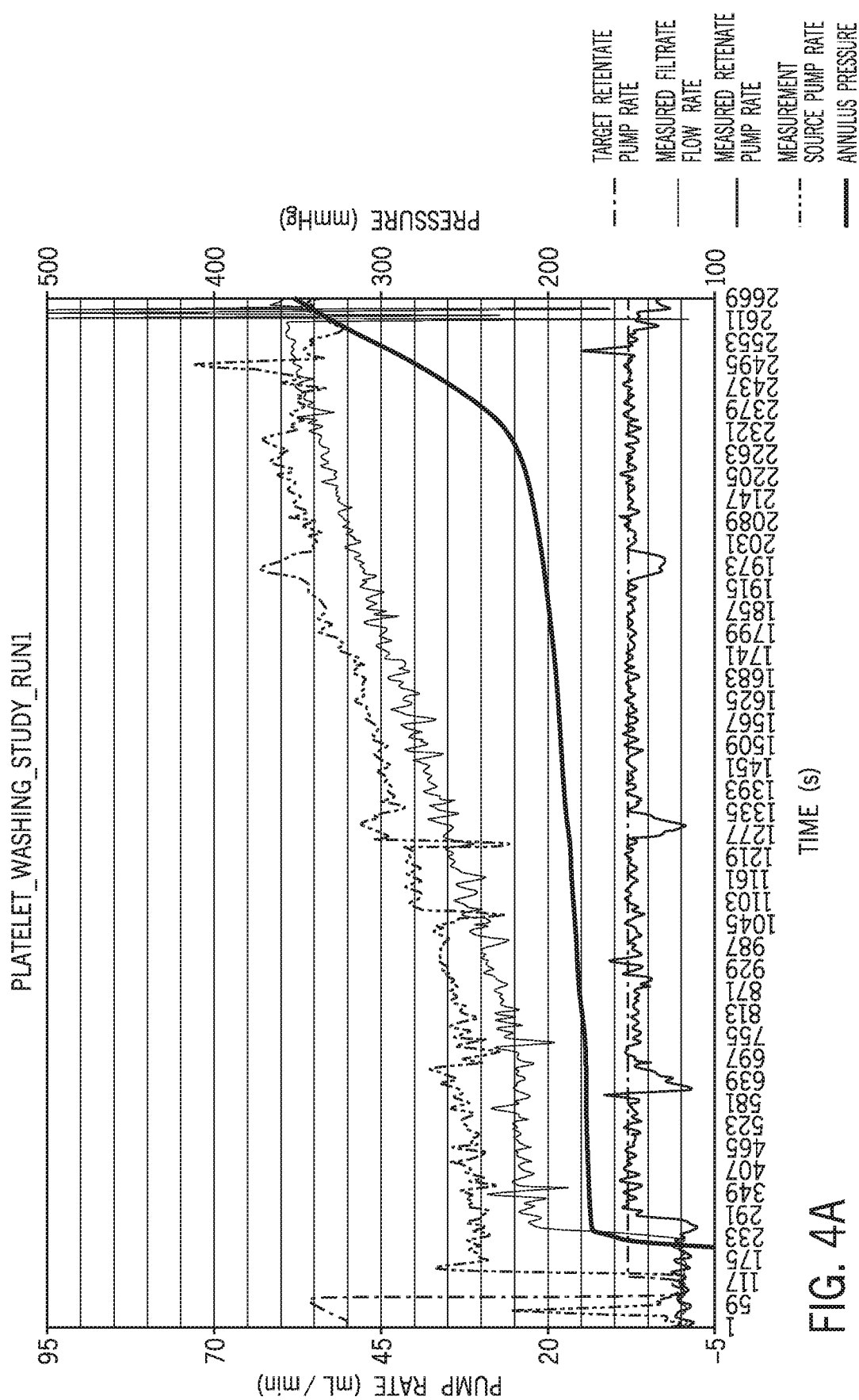
FIGS. 4A and 4B are graphs plotting annulus pressure and pump rates during two different fluid procedures plotted over time, according to an exemplary embodiment.

Also examined was whether the system was able to achieve the target platelet concentrations at the given spinner revolution rate without excessive membrane fouling or blockage of the membrane pores. One measure of membrane fouling is transmembrane pressure, obtained by measuring pressure within the gap 16 (FIG. 1) of the spinner, referred to as annulus pressure. FIG. 4A shows a graph of annulus pressure (blue curve) and pump rates during Run 1 plotted over time. The annulus pressure curve shows that annulus pressure gradually increased throughout most of the run and reached a peak of approximately 350 mm Hg at the end of Run 1. In an actual annulus pressure graph plotted over time, such as the graph of FIG. 4A, slope values at zero or approximately at zero may be preferable according to an exemplary embodiment.

Figure 4B:
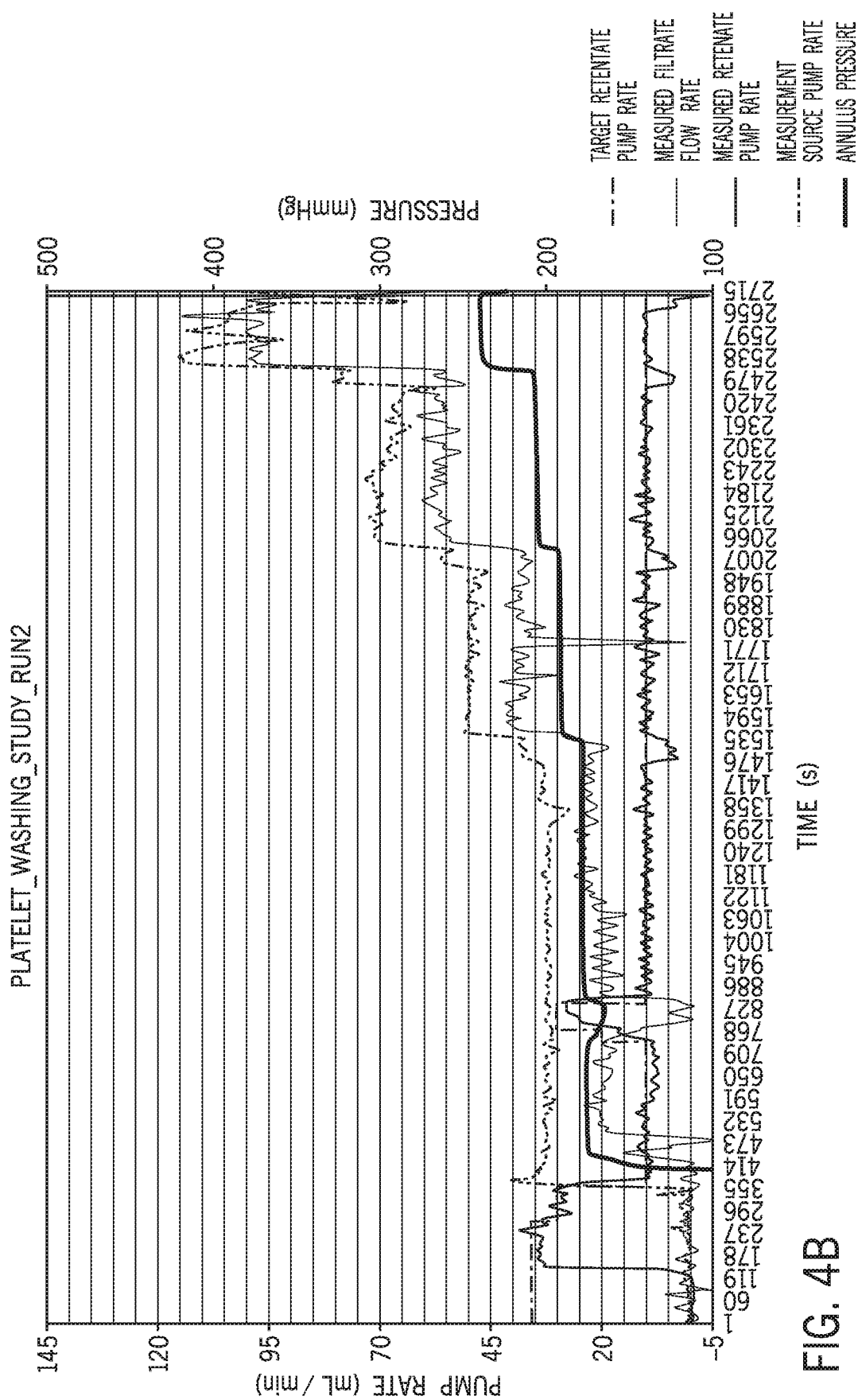

FIG. 4B shows a graph of annulus pressure and pump rates during Run 2 plotted over time. The annulus pressure curve (blue) shows that annulus pressure increased step-wise throughout the run and reached a peak of approximately 240 mm Hg at the end of Run 2. The graph shows that at all platelet concentrations, steady state annulus pressures were maintained and no uncontrolled fouling was observed.

Figure 5:
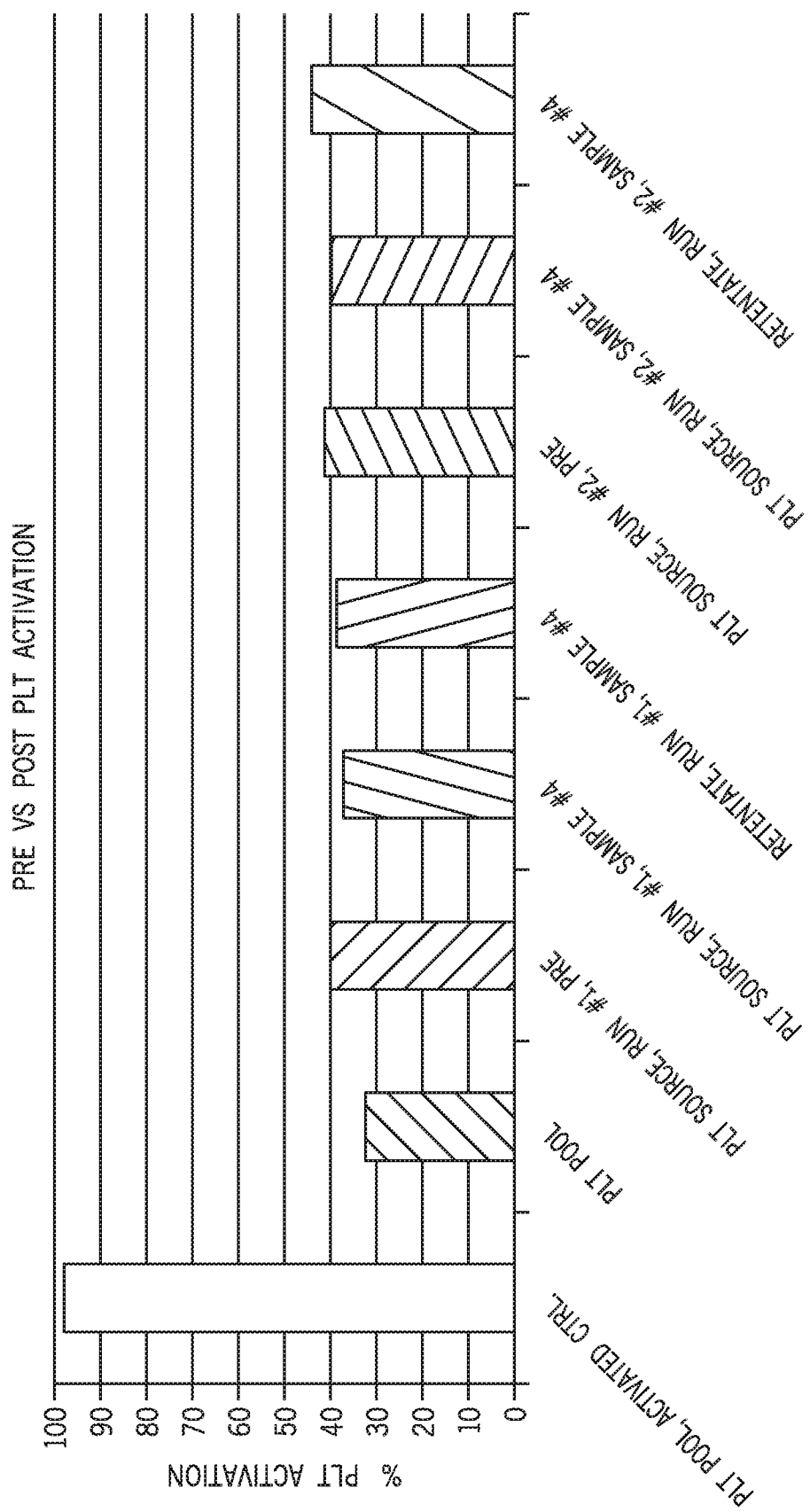
FIG. 5 is a bar chart for percent platelet activation at different points of each fluid procedure, according to an exemplary embodiment.

Also examined was the level of platelet activation as a result of the runs. It may be desirable to minimize platelet activation to prevent aggregation of platelets and maximize viable platelet product. FIG. 5 is a bar chart for percent platelet activation at different points of each run. The first bar "Plt Pool, Activated Ctrl." represents the level of platelet activation (almost 100%) for a control sample of activated platelets. The control sample was derived and later activated from the six same-type partial platelet units that were pooled together to form the initial 435 mL platelet pool. The second bar "Plt Pool" represents the level of platelet activation (~32%) for a control sample of platelets that were not deliberately activated. The "Plt Pool" control sample was also derived from the initial 435 mL platelet pool. The third bar "Plt Source, Run #1, Pre" represents the level of platelet activation (~40%) for a sample taken after passing pump 106 (FIG. 3) but prior to entering the separator during Run #1. The fourth bar "Plt Source, Run #1, Sample #4" represents the level of platelet activation (~37%) for a sample taken prior to entering the separator during the fourth phase of Run #1. The fifth bar "Retentate, Run #1, Sample #4" represents the level of platelet activation (~39%) for a retentate sample during the fourth phase of Run #1. The sixth bar "Plt Source, Run #2, Pre" represents the level of platelet activation (~40%) for a sample taken after passing pump 106 (FIG. 3) prior to entering the separator during Run #2. The seventh bar "Plt Source, Run #2, Sample #4" represents the level of platelet activation (~40%) for a sample taken prior to entering the separator during the fourth phase of Run #2. The eighth bar "Retentate, Run #2, Sample #4" represents the level of platelet activation (~43%) for a retentate sample during the fourth phase of Run #2.

The bars in FIG. 5 indicate that platelet activation levels for both Run #1 and Run #2 did not vary before and after the fluid procedures. For example, "Plt Source, Run #1, Pre" and "Plt Source, Run #2, Pre" prior to the fluid procedure show platelet activation levels of approximately 40%. In comparison, "Retentate, Run #1, Sample #4" and "Retentate, Run #2, Sample #4" after passing through the spinning membrane also show platelet activation levels of approximately 40%. Data shown in FIG. 5 therefore indicate that platelet activation levels were not significantly affected by the fluid procedures.

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

The invention claimed is:

1. A system for automated processing of a blood product, the system comprising:
   a reusable separation apparatus controlled by a microprocessing controller unit driven by software, wherein the apparatus and microprocessing controller unit are configurable with a plurality of settings;
   a disposable sterile circuit configured to associate with the reusable separation apparatus, the disposable sterile circuit comprising a spinning membrane separator comprising a porous membrane, wherein the separator comprises first and second outlets and an inlet configured to communicate with a source blood product comprising platelets having a first concentration of platelets and first volume;
   the reusable separation apparatus further comprising a source pump for controlling flow into the inlet and a retentate pump for controlling flow out of the second outlet;
   wherein the microprocessing controller is programmed to operate the apparatus to flow the source blood product into the inlet of the separator, separate an amount of supernatant of the source blood product from the first outlet into a filtrate container, and separate platelets and remaining supernatant from the second outlet into a retentate container; to collect the platelets and remaining supernatant in the retentate container at a second concentration of platelets and second volume, wherein the second concentration is greater than the first concentration and the second volume is less than the first volume;

the microprocessing controller being further programmed to operate the apparatus to concentrate the platelets in the source blood product in a single pass through the spinning membrane separator having a plurality of phases, wherein the source pump is operated at a target source pump rate value that increases with each successive phase, and the retentate pump is operated at a constant target retentate pump rate value in each phase, so that the concentration of platelets in the retentate exiting the second outlet increases from one phase to the next.

2. The system of claim 1, wherein the second concentration is within the range of $1000_E3$ to $3000_E3$ platelets per microliter.

3. The system of claim 1, wherein the second concentration is ten times that of the first concentration.

4. The system of claim 1, wherein the plurality of settings further comprises a target retentate pump rate value within the range of 8 to 10 ml/min, a spinner revolution rate of 2500 rpm, and a target source pump rate value within the range of 32 to 107 ml/min.

5. The system of claim 1, wherein the porous membrane is a polycarbonate membrane having a thickness of approximately 0.6 microns and a pore size of approximately 0.8 microns.

6. The system of claim 1, wherein the separator further comprises an annular gap within which annulus pressure is within the range of 150 to 350 mm Hg during separation of the source blood product.

7. The system of claim 1, wherein the source blood product prior to the flowing of the source blood product into the inlet of the separator comprises a percentage of activated platelets within the range of 30 to 45%, and the platelets collected in the retentate container also comprise a percentage of activated platelets within the range of 30-45%.

8. A method for automated processing of a blood product, the method comprising:

providing a reusable separation apparatus configured to associate with a disposable sterile circuit comprising a spinning membrane separator comprising a porous membrane in communication with a source blood product comprising platelets having a first concentration of platelets and first volume;

concentrating the platelets in the source blood product in a single pass through the spinning membrane separator having a plurality of phases by flowing the source blood product into an inlet of the separator at a first target rate value that increases with each successive phase;

separating an amount of supernatant of the source blood product from a first outlet of the separator into a filtrate container;

separating platelets and remaining supernatant from a second outlet of the separator into a retentate container at a second target rate value that is constant in each phase, wherein the platelets and remaining supernatant exiting the second outlet have a platelet concentration that increases from one phase to the next, and wherein the platelets and remaining supernatant in the retentate container have a second concentration of platelets and second volume in which the second concentration is greater than the first concentration and the second volume is less than the first volume.

9. The method of claim 8, wherein the second concentration is within the range of $1000_E3$ to $3000_E3$ platelets per microliter.

10. The method of claim 8, wherein the second concentration is ten times that of the first concentration.

11. The method of claim 8 further comprising: flowing the platelets and remaining supernatant from the second outlet of the separator into the retentate container at a second target rate value within the range of 8 to 10 ml/min, rotating the spinning membrane separator at a rate of 2500 rpm, and value flowing the source blood product into the inlet of the separator at a first target rate value within the range of 32 to 107 ml/min.

12. The method of claim 8, wherein the porous membrane is a polycarbonate membrane having a thickness of approximately 0.6 microns and a pore size of approximately 0.8 microns.

13. The method of claim 8, wherein the separator further comprises an annular gap within which annulus pressure is within the range of 150 to 350 mm Hg during separation of the source blood product.

14. The method of claim 8, wherein the source blood product prior to flowing the source blood product into the inlet of the separator comprises a percentage of activated platelets within the range of 30 to 45%, and the platelets collected in the retentate container also comprise a percentage of activated platelets within the range of 30-45%.

15. A method for automated processing of a blood product, the method comprising:

providing a reusable separation apparatus configured to associate with a disposable sterile circuit comprising a spinning membrane separator comprising a porous membrane and in communication with a source blood product comprising red blood cells, platelets and plasma;

flowing the source blood product into an inlet of the separator;

separating an amount of plasma and platelets of the source blood product from a first outlet of the separator into a first container, wherein the amount of plasma and platelets collected in the first container has a first platelet concentration and first volume;

separating red blood cells from a second outlet of the separator into a second container;

concentrating the platelets in the first container in a single pass through the spinning membrane separator having a plurality of phases by flowing the plasma and platelets derived from the first container into the inlet of the separator at a first target rate that increases with each successive phase;

separating an amount of plasma and flowing the separated plasma from the first outlet of the separator;

flowing platelets and remaining plasma from the second outlet of the separator into a third container at a second target rate value that is constant from one phase to the next, wherein the platelets and remaining plasma exiting the second outlet have a platelet concentration that increases from one to the next, and wherein the platelets and remaining supernatant in the third container have a second platelet concentration and second volume in which the second platelet concentration is greater than the first concentration and the second volume is less than the first volume.

16. The method of claim 15, wherein the second platelet concentration is within the range of $1000_E3$ to $3000_E3$ platelets per microliter.

17. The method of claim 15, wherein the second platelet concentration is ten times that of the first platelet concentration.

18. The method of claim 15 further comprising: flowing the platelets and remaining plasma from the first outlet of the separator at a second target rate value within the range of 8 to 10 ml/min, rotating the spinning membrane separator at a rate of 2500 rpm, and flowing the plasma and platelets derived from the first container into the inlet of the separator at a first target value within the range of 32 to 107 ml/min.

19. The method of claim 15, wherein during separating the platelets from the second outlet and the plasma from the first outlet, the separator comprises an annular gap within which annulus pressure is within the range of 150 to 350 mm Hg.

20. The method of claim 15, wherein the amount of plasma and platelets collected in the first container prior to flowing the amount of plasma and platelets into the inlet of the separator comprises a percentage of activated platelets within the range of 30 to 45%, and the platelets collected in the third container also comprise a percentage of activated platelets within the range of 30-45%.

* * * * *